US009211541B2

(12) United States Patent
Maeda et al.

(10) Patent No.: US 9,211,541 B2
(45) Date of Patent: Dec. 15, 2015

(54) NUCLEIC ACID AMPLIFICATION APPARATUS AND NUCLEIC ACID ANALYSIS APPARATUS

(75) Inventors: Kohshi Maeda, Tokyo (JP); Chie Sugiyama, Tokyo (JP); Yoshiyuki Shoji, Tokyo (JP); Masato Ishizawa, Tokyo (JP); Minoru Sano, Tokyo (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 0 days.

(21) Appl. No.: 14/123,824

(22) PCT Filed: May 31, 2012

(86) PCT No.: PCT/JP2012/064037

§ 371 (c)(1), (2), (4) Date: Dec. 4, 2013

(87) PCT Pub. No.: WO2012/176596

PCT Pub. Date: Dec. 27, 2012

(65) Prior Publication Data

US 2014/0093947 A1 Apr. 3, 2014

(30) Foreign Application Priority Data

Jun. 24, 2011 (JP) ................................ 2011-141107

(51) Int. Cl.

*C12M 3/00* (2006.01)
*B01L 7/00* (2006.01)

(52) U.S. Cl.

CPC ............. *B01L 7/52* (2013.01); *B01L 2200/148* (2013.01); *B01L 2300/024* (2013.01); *B01L 2300/0829* (2013.01); *B01L 2300/1822* (2013.01)

(58) Field of Classification Search

CPC ......... C12M 41/12; C12M 41/14; B01L 7/00; B01L 7/52; B01L 2300/18; B01L 2300/1805

See application file for complete search history.

(56) References Cited

U.S. PATENT DOCUMENTS 5,138,872 A 8/1992 Henderson
5,455,008 A * 10/1995 Earley et al. .................. 422/511

(Continued)

FOREIGN PATENT DOCUMENTS

JP 3-131761 A 6/1991
JP 05-317030 A 12/1993

(Continued)

OTHER PUBLICATIONS

English translation of JP 2010-51265, Hayashida et al, 2010.*

(Continued)

*Primary Examiner* — Nathan Bowers
(74) *Attorney, Agent, or Firm* — Mattingly & Malur, PC

(57) ABSTRACT

According to a conventional technique, when a calibrated temperature measuring probe is used for correcting the temperature absolute values of individually temperature-controllable thermal control blocks, a temperature difference of a maximum of 0.5° C. remains between the thermal control blocks. According to the present invention, the melting temperature of a temperature calibration sample housed in a reaction vessel corresponding to each of the temperature control blocks is measured as a measured melting temperature. The measured melting temperature corresponding to each of the thermal control blocks and the reference melting temperature of the temperature calibration sample are compared, and the temperature absolute value of each of the thermal control blocks is corrected based on respective difference values.

4 Claims, 15 Drawing Sheets

(56) References Cited

U.S. PATENT DOCUMENTS

| | | | | |
|---|---|---|---|---|
| 5,779,981 | A * | 7/1998 | Danssaert et al. | 422/67 |
| 5,972,715 | A | 10/1999 | Celentano et al. | |
| 2003/0143574 | A1 | 7/2003 | Squirrell et al. | |
| 2004/0081974 | A1 | 4/2004 | Gao | |
| 2008/0280350 | A1 | 11/2008 | Moriwaki et al. | |
| 2009/0258412 | A1 | 10/2009 | Moriwaki et al. | |
| 2010/0184067 | A1 | 7/2010 | Abe et al. | |
| 2012/0178077 | A1* | 7/2012 | DeCastro et al. | 435/3 |
| 2012/0264203 | A1* | 10/2012 | Dinges | 435/287.2 |

FOREIGN PATENT DOCUMENTS

| | | | |
|---|---|---|---|
| JP | 10-206411 | A | 8/1998 |
| JP | 2003-525621 | A | 9/2003 |
| JP | 2005-519642 | A | 7/2005 |
| JP | 2008-278810 | A | 11/2008 |
| JP | 2008-278896 | A | 11/2008 |
| JP | 2009-254260 | A | 11/2009 |
| JP | 2010-051265 | A | 3/2010 |
| JP | 2010-166823 | A | 8/2010 |
| WO | 98/43740 | A2 | 10/1998 |

OTHER PUBLICATIONS

Tajiri-Utagawa et al., "Development of a Rapid High-Throughput Method for High-Resolution Melting Analysis for Routine Detection and Genotyping of Noroviruses", Journal of Clinical Microbiology, Feb. 2009, pp. 435-440, vol. 47, No. 2.

* cited by examiner

Before correction: Max temperature difference 1.7°C

After correction by embodiment: Max temperature difference 0.1°C or less

After correction by conventional example: Max temperature difference 0.53°C

NUCLEIC ACID AMPLIFICATION APPARATUS AND NUCLEIC ACID ANALYSIS APPARATUS

TECHNICAL FIELD

The present invention relates to a nucleic acid amplification system including a plurality of individually temperature-controllable thermal control blocks, and to a genetic testing system using the nucleic acid amplification system as a part of the system.

BACKGROUND ART

A thermal control block needs to accurately control the absolute value of its temperature to a target temperature. Conventionally, for measuring the absolute value of the thermal control block temperature, a method is adopted whereby a calibrated temperature measuring probe is used, and, if the measured temperature differs from the target temperature, correction is made so that the measured temperature matches the target temperature. Generally, it is considered that the limit precision of temperature correction using the calibrated temperature measuring probe is ±0.25° C.

A plurality of individually temperature-controllable thermal control blocks may be provided in a system. In this case, too, when the temperature of the temperature control blocks is individually corrected by using the calibrated temperature measuring probe, the temperature control precision of the thermal control blocks after correction is ±0.25° C. Thus, theoretically, the maximum temperature difference between the thermal control blocks is 0.5° C.

Meanwhile, for temperature correction of the thermal control blocks, a method involving a test strip with the use of a liquid crystal of heat discoloration is proposed (see Patent Document 1, for example). According to the method, in principle, a liquid crystal of heat discoloration is mixed in a test strip that is contacted with a fluid sample, and the test strip temperature is calibrated by detecting discoloration of the liquid crystal when the test strip is controlled to a testing temperature.

PRIOR ART DOCUMENTS

Patent Documents

Patent Document 1: JP Patent (Kokai) Publication No. 10-206411 (1998) A

Patent Document 2: JP Patent (Kokai) Publication No. 2010-51265 A

Patent Document 3: JP Patent (Kokai) Publication No. 05-317030 (1993) A

Patent Document 4: JP Patent (Kokai) Publication No. 2010-166823 A

Patent Document 5: JP Patent (Kohyo) Publication No. 2003-525621 A

Patent Document 6: JP Patent (Kohyo) Publication No. 2005-519642 A

Patent Document 7: JP Patent (Kokai) Publication No. 2008-278896 A

Patent Document 8: JP Patent (Kokai) Publication No. 03-131761 (1991) A

Non-Patent Document

Non-Patent Document 1: JOURNAL OF CLINICAL MICROBIOLOGY, February 2009, p. 435-440

SUMMARY OF INVENTION

Problem to be Solved by Invention

Some of the reactions for which temperature management is conducted by using the thermal control blocks require particularly precise temperature control. Examples are reactions associated with polymerase chain reaction (PCR) and high resolution melting (HRM) analysis.

The PCR process is a nucleic acid amplification method whereby a target nucleic acid sequence is amplified by a factor of $2^n$ by repeating (1) a denaturing temperature of 95° C.; (2) an annealing temperature on the order of 55° C. to 65° C.; and (3) an extension temperature, alternately n times (hereafter referred to as a "thermal cycle").

The annealing temperature and the extension temperature vary depending on the target sequence, and the required precision of the temperatures is generally considered to be within ±0.5° C. The higher the temperature accuracy and reproducibility, the greater the improvement in DNA amplification efficiency and amplification reproducibility.

The amplification efficiency and the amplification reproducibility are important factors that affect the quantitative precision of a real-time PCR process. The real-time PCR process refers to a method by which PCR amplification is measured in real-time by using a fluorescence dye in order to quantify the amount of nucleic acid in the reaction solution based on the fluorescence intensity and the number of cycles.

Conventionally, for quantifying DNA by the real-time PCR process, a real-time PCR system of a type such that a plurality of reaction vessels (wells) are disposed in a space whose temperature is managed by a single thermal control block is used. When the reaction vessels (wells) are temperature-managed by the single temperature control block, the temperature difference between the reaction vessels (wells) can be limited to ±0.2° C. or less.

In recent years, a real-time PCR system with a plurality of thermal control blocks has been proposed. The real-time PCR system can control the temperature of the thermal control blocks individually, and perform a plurality of thermal cycles simultaneously. Obviously, in this type of system, too, the same level of temperature control precision is required between the reaction vessels (wells) as when only a single thermal control block is used.

Meanwhile, the high resolution melting (HRM) analysis is an analysis method of determining the melting temperature (temperature at which the double stranded bond of an amplified double stranded nucleic acid is melted) of an amplification product amplified by PCR process by fluorescence-measuring the temperature of the amplification product in a range of approximately 60° C. to 95° C. with the resolution of 0.1° C. or less.

The melting temperature differs from one target amplification sequence to another, and is known to differ, theoretically, depending on even a single base. By this analysis method, nucleic acids can be separately detected from an amplified reaction solution containing a plurality of different sequences on a sequence by sequence basis.

For the purpose of comparing the difference in melting temperature of sample groups placed in a plurality of reaction vessels (wells), the higher the temperature reproducibility between the reaction vessels (wells), the better, and the required temperature reproducibility between the reaction wells for the analysis method is ±0.1° C. or less.

Currently, the real-time PCR system is beginning to be applied for clinical tests. For example, there is a fully automatic clinical test apparatus that performs real-time PCR by using a plurality of thermal control blocks. In the apparatus, analysis performance is influenced by the difference in temperature absolute values between the thermal control blocks. Thus, the same level of temperature control precision as the temperature control precision between the reaction vessels (wells) is required between the thermal control blocks.

However, in the conventional temperature correction method that employs the calibrated temperature measuring probe, a temperature difference of a maximum 0.5° C. remains, and it is difficult to satisfy the above requirements.

Solution to Problem

In order to solve the technical problem, the inventors conducted the following measurement. First, one type of nucleic acid fragments amplified by PCR process was put together in the same vessel and mixed well. The mixture was then dispensed into 96 reaction vessels (wells), as illustrated in FIG. 1A. Next, by using a real-time PCR system with the temperature uniformity between the reaction vessels (wells) of 0.05° C. or less, the nucleic acid fragments were subjected to HRM analysis and the melting temperature was measured. As a result, the inventors found that, as illustrated in FIG. 1B, the melting temperature variations of the nucleic acid fragments amplified by PCR were very small and within ±0.05° C.

The inventors, utilizing this discovery, provides a nucleic acid amplification system with a plurality of individually temperature-controllable thermal control blocks; a real-time fluorescence measuring unit that performs real-time fluorescence measurement on a sample in a reaction vessel temperature-managed by the thermal control blocks; a storage unit that stores a reference melting temperature of a temperature calibration sample dispensed in one or a plurality of reaction vessels temperature-managed by the thermal control blocks; a melting temperature measurement unit that measures a melting temperature of the temperature calibration sample housed in the reaction vessel corresponding to each of the thermal control blocks as a measured melting temperature; and a temperature correction unit that compares the measured melting temperature corresponding to each of the thermal control blocks with the reference melting temperature, and that corrects a temperature absolute value of each of the temperature control blocks based on a difference value. The inventors also implement a nucleic acid amplification system of the above configuration in a genetic testing system.

Effects of Invention

According to the present invention, the temperature uniformity between a plurality of individually temperature-controllable thermal control blocks can be realized with the same level of precision as the temperature control resolution.

Other problems, configurations, and effects will become apparent from a reading of the following description of embodiments.

MODES FOR CARRYING OUT THE INVENTION

In the following, embodiments of the present invention will be described with reference to the drawings. The embodiments of the present invention are not limited to the following embodiments, and various modifications may be made within the technical scope of the invention.

<Embodiment 1>

(Functional Block Configuration of Nucleic Acid Amplification System)

Figure 2:
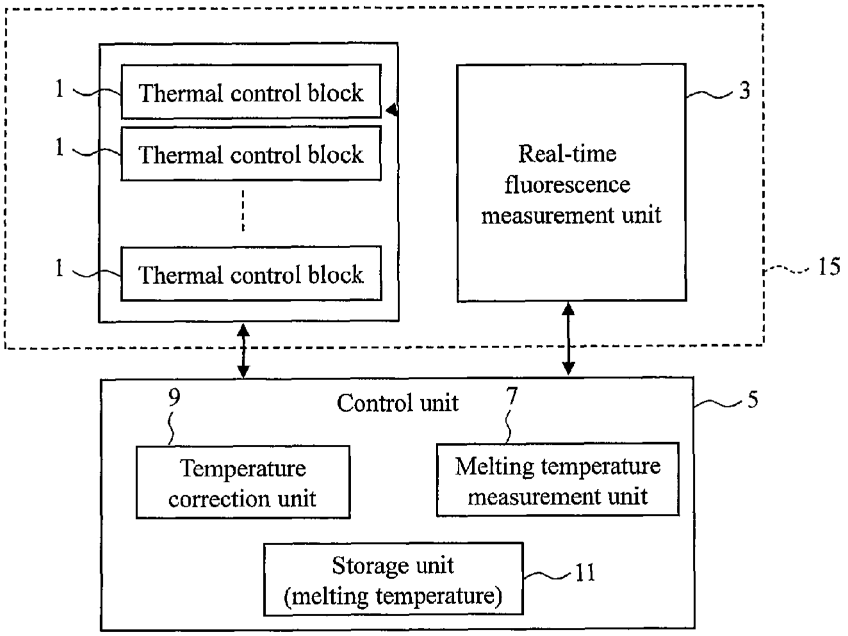
FIG. 2 shows a functional block configuration of a nucleic acid amplification system incorporating a real-time fluorescence measurement mechanism.

FIG. 2 illustrates a functional block configuration of a nucleic acid amplification system according to an embodiment. The nucleic acid amplification system illustrated in FIG. 2 includes a plurality of individually temperature-controllable thermal control blocks 1, a real-time fluorescence measuring unit 3, and a control unit 5 that controls these blocks. In the present specification, a mechanism portion including the individually temperature-controllable thermal control blocks 1 and the real-time fluorescence measuring unit 3 will be referred to as a real-time fluorescence measurement mechanism 15.

The temperature control blocks 1 include a base member of a material with excellent thermal conductivity, with a reaction vessel housed in a retention mechanism formed on the base member. On the base member, a temperature sensor and a heat source are also disposed. For the base member, copper, aluminum, or various alloys may be used. For the temperature sensor, a thermistor, a thermocouple, or a resistance temperature detector is used, for example. The temperature sensor measures the temperature of a sample in the reaction vessel and is therefore disposed in the vicinity of the retention mechanism of the reaction vessel.

For the heat source, a Peltier element is used, for example. The Peltier element, which is a thermoelectric element, is used for heating or cooling the base member. In a preferred configuration, a radiating fin is disposed on the heat source. The heat source may not be provided in the thermal control blocks 1 as long as temperature control is enabled. For example, an air incubator system is adopted to control the temperature of the thermal control blocks 1 by changing air temperature.

The thermal control blocks 1 are disposed on a mount made of a material with excellent thermal insulation properties, such as plastics. Thus, the diffusion of temperature from one thermal control block 1 to another thermal control block 1 can be disregarded. Namely, the mutual temperature interference between the thermal control blocks can be disregarded.

The real-time fluorescence measuring unit 3 performs real-time fluorescence measurement of a sample in the reaction vessel whose temperature is managed by each of the thermal control blocks 1. Obviously, the sample is fluorescence-labeled. The real-time fluorescence measuring unit 3 includes an excitation light source that generates excitation light with which the reaction vessel is irradiated, and a fluorescence detector that measures fluorescence generated from the sample irradiated with the excitation light. For the excitation light source, a light-emitting diode (LED), a semiconductor laser, a xenon lamp, or a halogen lamp is used, for example. For the fluorescence detector, a photodiode, a photomultiplier, or a CCD is used, for example.

Temperature control of the thermal control blocks 1, processing of measurement data of the real-time fluorescence measuring unit 3, and the like are performed by the control unit 5. In the case of the illustrated embodiment, the control unit 5 stores the melting temperature of a temperature calibration sample used during the temperature correction of the thermal control blocks 1 in a storage unit 11. The melting temperature (which may be hereafter referred to as a “reference melting temperature”) may be fed to the control unit 5 through various routes, as will be described below.

The control unit 5 includes a melting temperature measurement unit 7 and a temperature correction unit 9 as functions used during temperature correction of the thermal control blocks 1.

The melting temperature measurement unit 7 measures the melting temperature of the temperature calibration sample housed in each reaction vessel corresponding to the respective thermal control blocks 1. The melting temperature is determined as the measured temperature (which may be hereafter referred to as a “measured melting temperature) from the temperature sensor upon detection of melting of the temperature calibration sample by the real-time fluorescence measuring unit 3. The measured melting temperature is fed from the melting temperature measurement unit 7 to the temperature correction unit 9.

The temperature correction unit 9 compares the measured melting temperature with the reference melting temperature stored in the storage unit 11, and corrects the temperature absolute value of each of the thermal control blocks 1 such that the difference is eliminated. The difference between the measured melting temperature detected for each of the thermal control blocks 1 and the reference melting temperature provides the temperature control precision of the thermal control blocks 1.

(Specific Example 1 of Apparatus Configuration)

Figure 3:
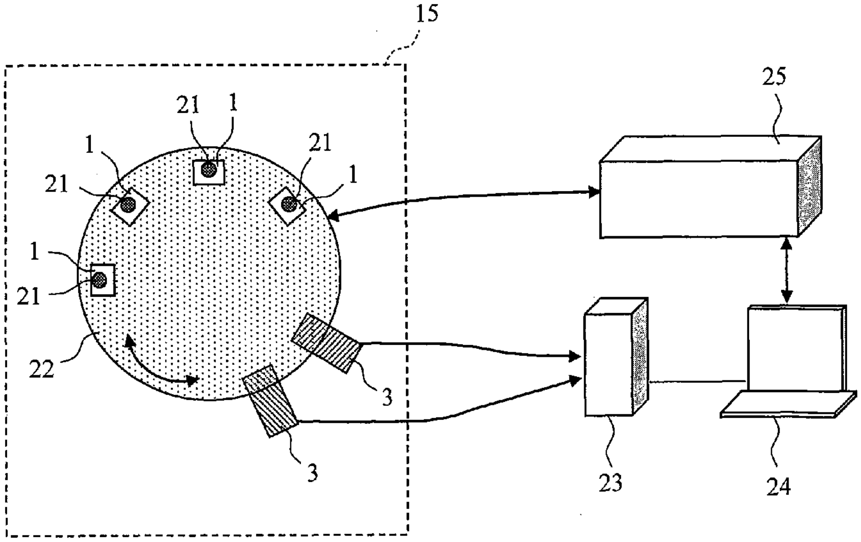
FIG. 3 illustrates an embodiment of the nucleic acid amplification system incorporating the real-time fluorescence measurement mechanism.

FIG. 3 illustrates a specific example of the nucleic acid amplification system in which the temperature absolute values of the thermal control blocks 1 are corrected by using a single type of temperature calibration sample. The apparatus configuration illustrated in FIG. 3 is a detailed representation of the apparatus configuration illustrated in FIG. 2.

In the case of the present embodiment, four individually temperature-controllable temperature control blocks 1 are disposed along the outer edge of a disc-shaped rotary disc 22. The rotary disc 22 corresponds to the mount of Embodiment 1. The rotary disc 22 is made of a material with excellent thermal insulation properties. Thus, the mutual temperature interference between the thermal control blocks can be disregard.

The rotary disc 22 is fixed onto a rotating shaft, which is not shown, and is configured to be freely rotatable in both clockwise and anticlockwise directions, as indicated by arrows. The rotating shaft is rotated by a stepping motor, which is not shown.

On the thermal control blocks 1, one or a plurality of reaction vessels 21 are detachably housed or mounted. The reaction vessels 21 are of a material transparent to light of a fluorescence wavelength band, with a bottom portion exposed from a rear surface side of the rotary disc 22.

The real-time fluorescence measuring unit 3 is disposed on the rear surface side of the rotary disc 22 and irradiates the excitation light generated from the excitation light source onto the bottom portion of the reaction vessels 21. The real-time fluorescence measuring unit 3 also detects fluorescence produced by the sample in the reaction vessels 21 irradiated with the excitation light, by using the fluorescence detector, and outputs the intensity of the fluorescence to the data processing unit 23 as fluorescence measurement data. In the case of FIG. 3, two real-time fluorescence measuring units 3 are provided. Thus, the real-time fluorescence measurement can be performed for two reaction vessels 21 simultaneously.

The data processing unit 23 processes the fluorescence measurement data successively inputted from the fluorescence detector, and temperature data measured by the temperature sensor, and outputs an outcome to the storage/operating unit 24.

The storage/operating unit 24 includes a general-purpose computer, for example, and performs an analysis process for analyzing the melting temperature of each of the temperature blocks 1 and an operating process for calculating a correction value. The storage/operating unit 24 determines, based on the fluorescence measurement data, the temperature measured at the point of time when the melting of the temperature calibration sample is detected as the measured melting temperature. The storage/operating unit 24 also calculates a temperature absolute value correction value based on the difference value between the measured melting temperature and the reference melting temperature. The measured temperature of the thermal control blocks 1 is also fed to the system control unit 25. The reference melting temperature is stored in the storage/operating unit 24 in advance.

The system control unit 25 controls each of the thermal control blocks 1 to a target temperature so that a temperature change necessary for real-time fluorescence detection can be obtained. Specifically, the amount of heat generated by the heat source provided in the thermal control blocks 1 is controlled. The system control unit 25 acquires the measured temperature from the temperature sensor provided in the thermal control blocks 1, and implements feedback control such that the measured temperature matches the target temperature. The measured temperature is also fed to the storage/operating unit 24, as described above.

At the time of real-time fluorescence detection, the system control unit 25 varies the temperature of the reaction vessels 21 at least in a range of 50° C. to 95° C. The data processing unit 23, the storage/operating unit 24, and the system control unit 25 illustrated in FIG. 3 correspond to the control unit 5 of FIG. 2. While in FIG. 3 the data processing unit 23, the storage/operating unit 24, and the system control unit 25 are illustrated as independent devices, they may be configured as a single apparatus.

In the foregoing description, the temperature control blocks 1 are mounted at the outer edge of the rotary disc 22, and fluorescence is detected when the thermal control blocks 1 are passed in front of the real-time fluorescence measuring units 3 as the rotary disc 22 is rotated.

However, the real-time fluorescence measuring units 3 may be configured to be rotated or moved while the mount on which the thermal control blocks 1 are mounted are fixed. In this case, fluorescence detection is performed when the real-time fluorescence measuring units 3 pass the positions opposite the thermal control blocks 1.

(Specific Example 2 of Apparatus Configuration)

Figure 4:
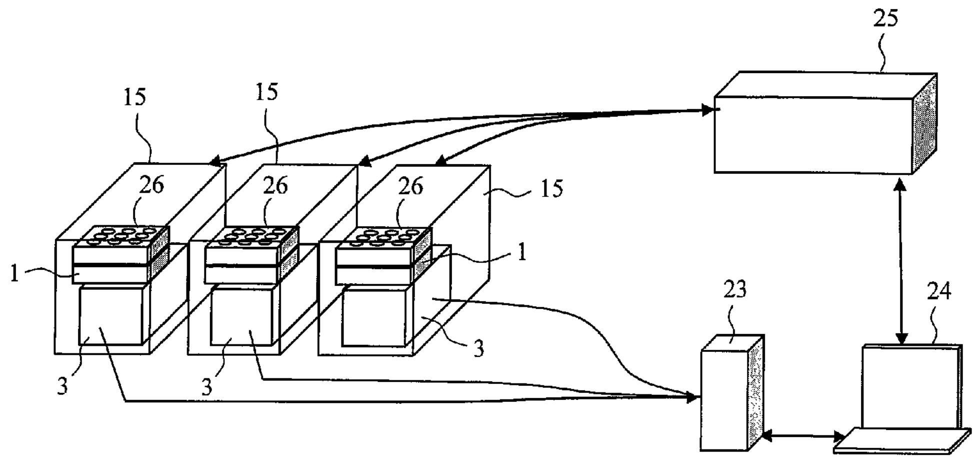
FIG. 4 illustrates an embodiment of the nucleic acid amplification system incorporating the real-time fluorescence measurement mechanism.

FIG. 4 illustrates another apparatus configuration example of the nucleic acid amplification system for correcting the temperature of the thermal control blocks 1 by using a single type of temperature calibration sample. The apparatus configuration illustrated in FIG. 4 is also a detailed representation of the apparatus configuration of FIG. 2.

In the case of the apparatus configuration illustrated in FIG. 3, the number of the real-time fluorescence measuring units 3 is smaller than the number of the thermal control blocks 1. For this reason, either the mount on which the thermal control blocks 1 are mounted or the real-time fluorescence measuring units 3 is fixed, while the other is rotation-controlled.

However, the temperature control blocks 1 and the real-time fluorescence measuring units 3 may be paired on a one-to-one basis, and a plurality of such pairs may be provided in an apparatus configuration as illustrated in FIG. 4. In the case of FIG. 4, the thermal control blocks 1 include reaction plates 26 with a plurality of reaction vessels 21 arranged in a matrix.

(Reaction Vessel)

In the case of the present embodiment, the reaction vessels 21 and the reaction plates 26 may be of any material or shape as long as the reaction vessels 21 and the reaction plates 26 can transmit fluorescence wavelengths and conduct the heat from the thermal control blocks 1. More preferably, a PCR tube (Greiner, Germany) that is free of DNase or RNase, or a 96 well PCR plate may be used.

(Temperature Calibration Sample)

The temperature calibration sample according to the present embodiment may contain a HRM-analyzable nucleic acid fragment and a detection dye. As the nucleic acid fragment, DNA, RNA, or PNA may be used. More preferably, a sample obtained by amplifying any desired single type of nucleic acid fragment by PCR process may be used. Further preferably, a nucleic acid fragment such that matching between the absolute temperature of an aqueous solution and melting temperature has been confirmed may be used.

When two types of nucleic acid fragments are used as according to an embodiment described below, two types of HRM-analyzable nucleic acid fragments and a detection dye may be contained. More preferably, an amplification product obtained by amplifying two types of nucleic acid fragments individually by PCR may be used.

Preferably, the temperature calibration sample may be housed in a vessel with a bar-code affixed onto an outer wall thereof. Preferably, the bar-code may include information about at least melting temperature information of the temperature calibration sample. When a plate-type reaction vessel in which the temperature calibration sample is already dispensed (i.e., the reaction plates 26) is used, the bar-code may be affixed onto the reaction plates 26 themselves. Of course, the bar-code information may preferably include at least the melting temperature information of the temperature calibration sample.

(Outline of Temperature Absolute Value Correction Operation)

The nucleic acid amplification system according to the present embodiment corrects temperature absolute value variations that exist between a plurality of thermal control blocks through three process steps described below.

(Step 1)

A sample containing a nucleic acid fragment with a predetermined melting temperature that has been amplified by a nucleic acid amplification process, such as PCR process, is dispensed into a plurality of reaction vessels as a temperature calibration sample. Thereafter, the reaction vessels are placed or mounted on the retention mechanism of the temperature control blocks 1 in the nucleic acid amplification system for temperature calibration. Alternatively, the temperature calibration sample is dispensed into the reaction vessels pre-placed or pre-mounted on the retention mechanism of the thermal control blocks 1.

(Step 2)

Next, the melting temperature of the temperature calibration sample is actually measured in each of the thermal control blocks 1. For measuring the melting temperature, a known method may be used. For example, fluorescence intensity is measured in real-time while the temperature of the thermal control blocks 1 is changed from a low temperature (such as 60° C.) to a high temperature (such as 95° C.). At this time, the fluorescence intensity is measured while the temperature is changed with the same or higher order of temperature resolution than the temperature precision required from the nucleic acid amplification system. For example, when the temperature precision required from the nucleic acid amplification system is ±0.1° C. or less, the target temperature is varied at the increments of 0.1° C. or less when the melting temperature is measured by fluorescence.

(Step 3)

When the measurement of the melting temperature is completed, the control unit 5 corrects the temperature absolute values managed for the thermal control blocks 1 such that the melting temperature measurement values match the melting temperature stored in the storage unit 11. During the melting temperature measurement, a measurement error may be introduced. Thus, in a more preferred embodiment, steps 2 and 3 may be repeated two or more times so as to increase the temperature uniformity between the thermal control blocks.

(Details of Correction Operation)

Figure 5:
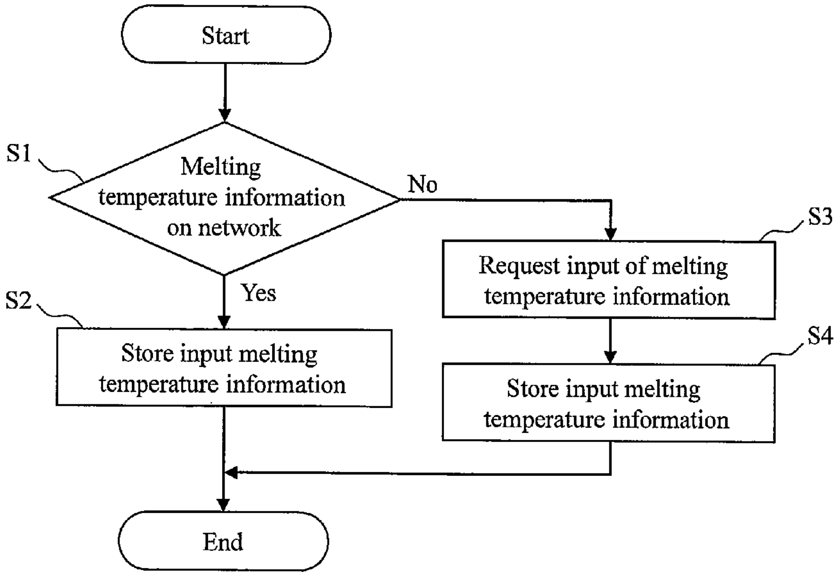
FIG. 5 is a diagram for explaining a procedure of confirming melting temperature information of a temperature calibration sample.

FIG. 5 shows a process procedure for confirming melting temperature information that is implemented prior to temperature correction. In the present example, the process is performed by the storage/operating unit 24. Alternatively, the process may be performed by another control unit of the nucleic acid amplification system, or an external control unit connected to the nucleic acid amplification system.

First, the storage/operating unit 24 attempts to obtain the melting temperature information of the temperature calibration sample via a network (step S1). If it is obtainable, the storage/operating unit 24 reads the melting temperature information via the network, and stores the information in a predetermined storage area (step S2). The network herein may include the Internet as well as a LAN.

On the other hand, when the relevant information is not available on the network, or when the storage/operating unit 24 is not connected to the network, the storage/operating unit 24 requests the input of the melting temperature information from a user (step S3). In this case, the user inputs the melting temperature by using a keyboard, a bar-code, and the like. The storage/operating unit 24 stores the inputted melting temperature information in the predetermined storage area (step S4).

Figure 6:
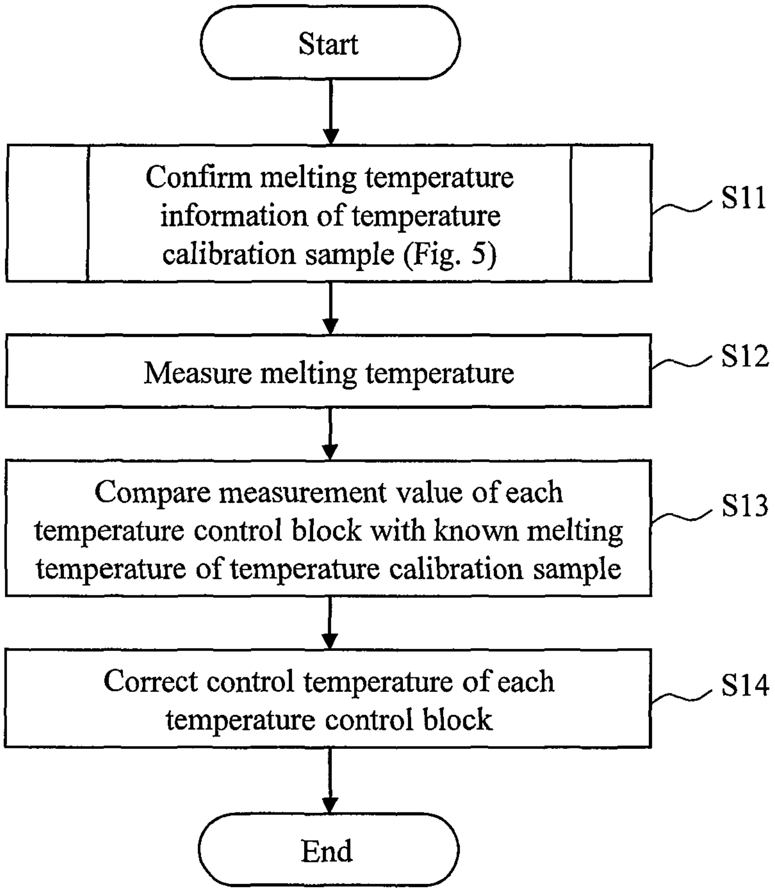
FIG. 6 is a diagram for explaining a temperature correction operation.

FIG. 6 illustrates the temperature correction operation as a whole including the melting temperature information confirmation process (FIG. 5). In the following description, a series of processes is performed by the storage/operating unit 24. However, the series of processes may be performed by another control unit of the nucleic acid amplification system, or an external control unit connected to the nucleic acid amplification system.

When the temperature calibration of the nucleic acid amplification system is started, the storage/operating unit 24 confirms the melting temperature information of the temperature calibration sample (step S11). Herein, the processing operation illustrated in FIG. 5 is performed.

Next, the storage/operating unit 24 measures the melting temperature of the mounted temperature calibration sample (step S12). Specifically, the temperature of the thermal control blocks 1 is changed from a low temperature (such as 60° C.) to a high temperature (such as 95° C.) at predetermined temperature increments, and the intensity of fluorescence emitted from the temperature calibration sample is measured in real-time. The storage/operating unit 24, upon detection of melting of the sample based on the fluorescence intensity, stores the instantaneous measured temperature in a predetermined storage area as the measured melting temperature.

The storage/operating unit 24 next compares a previously confirmed reference melting temperature with the measured melting temperature of each of the thermal control blocks 1 (step S13). At this time, the storage/operating unit 24 calculates a difference value between the previously confirmed reference melting temperature and the measured melting temperature of each of the thermal control blocks 1.

The storage/operating unit 24, by using the difference value calculated for each of the thermal control blocks 1, corrects the temperature absolute value of each thermal control block such that the measured melting temperature of each of the thermal control blocks 1 matches the reference melting temperature of the temperature calibration sample (step S14).

In the following, a melting temperature curve obtained by measuring the melting temperature with the resolution of 0.1° C. or less when using the thermal control blocks 1 in which temperature can be set with the resolution of 0.1° C. or less and the temperature calibration sample with the melting temperature of 87.3° C. will be described.

In the case of the present embodiment, the melting temperature of the sample housed in each reaction vessel is determined as the temperature at the fluorescence intensity value (0.2) with the greatest attenuation rate (the amount of decrease in fluorescence intensity per unit time). However, the method of determining the melting temperature is not limited to this method. For example, an analysis method according to Non-patent Document 1 can be used.

Figure 7A:
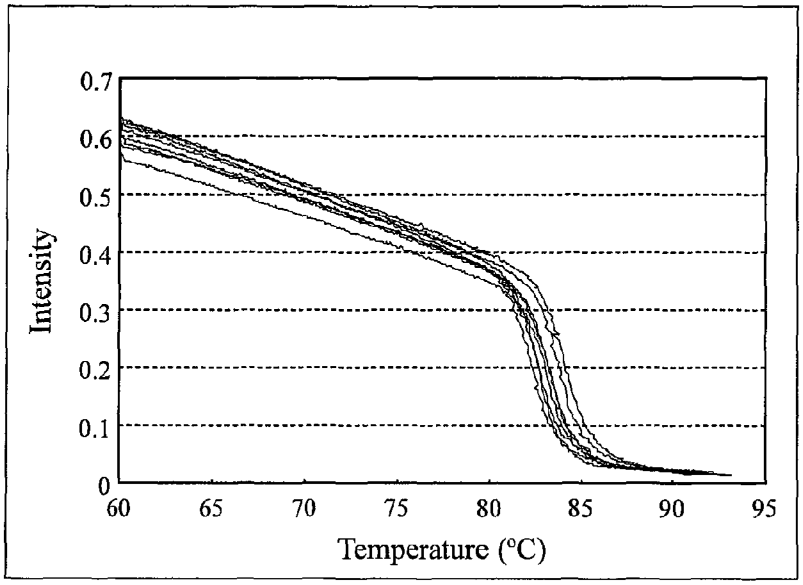
FIG. 7A shows a measurement result in a case where temperature correction is not implemented (before correction).

FIG. 7A shows an example of measurement of the melting temperature curve for the thermal control blocks 1 when no temperature correction is performed at all. In this example, the maximum temperature difference between the plurality of thermal control blocks was 1.7° C. In FIG. 7A, the measurement values are plotted, with the horizontal axis showing the temperature and the vertical axis showing the fluorescence intensity. The same applies to FIGS. 7B and 7C.

Figure 7B:
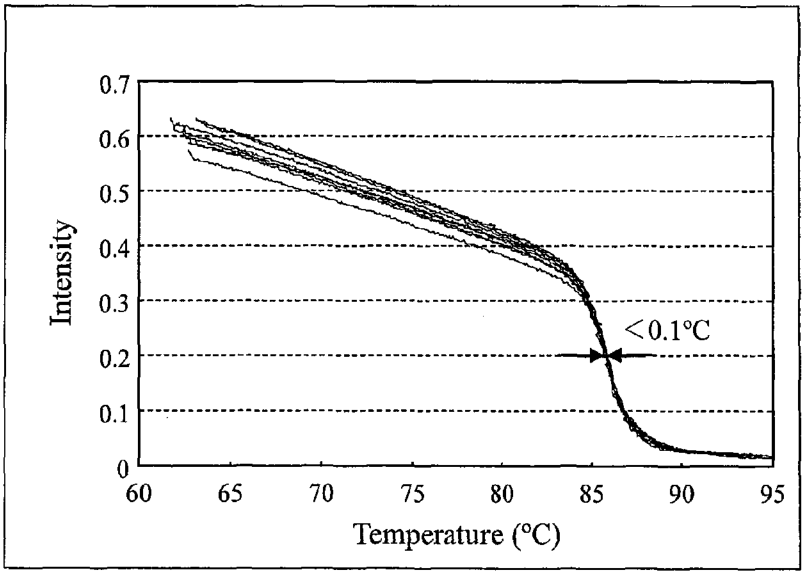
FIG. 7B shows a measurement result in a case where the temperature absolute value of each temperature control block was corrected with reference to the melting temperature.

FIG. 7B shows an example of measurement of the melting temperature curve for the thermal control blocks 1 when the temperature absolute value of each of the temperature control blocks 1 was corrected with reference to the melting temperature of 87.3° C. as a reference. In this example, it can be seen that the maximum temperature difference between the thermal control blocks is converged at 0.1° C. or less.

Figure 7C:
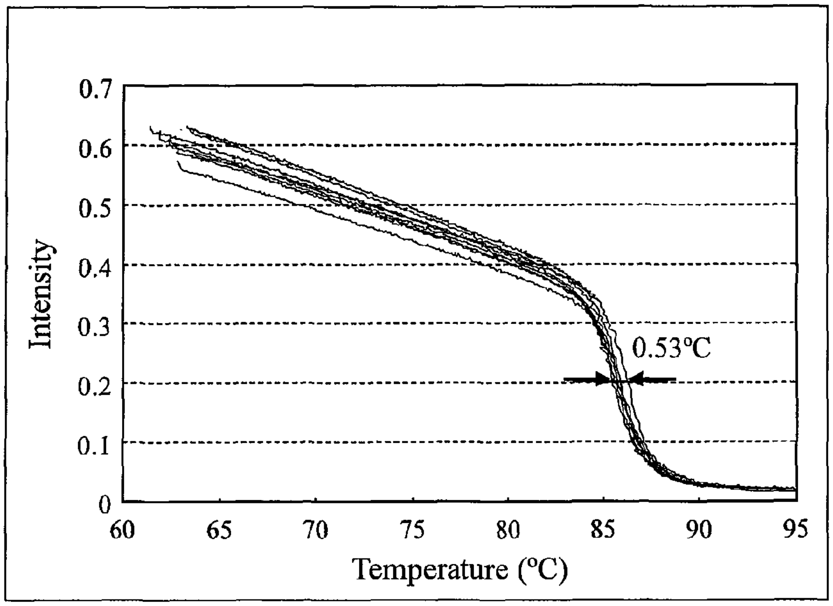
FIG. 7C shows a measurement result in a case where the temperature absolute value of each thermal control block was corrected by using a calibrated temperature measuring probe (conventional example).

For reference purposes, an example of measurement of the melting temperature curve for the thermal control blocks 1 when a conventional temperature setting method using a calibrated temperature probe was used is shown in FIG. 7C. In this example, the maximum temperature difference between the thermal control blocks was 0.53° C.

(Summary)

Figure 1A:
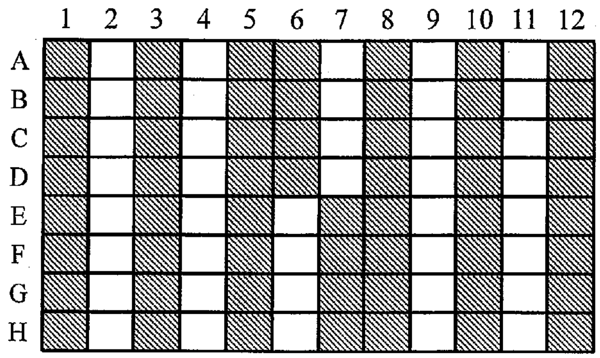
FIG. 1A illustrates an example of dispensing of a temperature calibration sample into reaction vessels (wells).
Figure 1B:
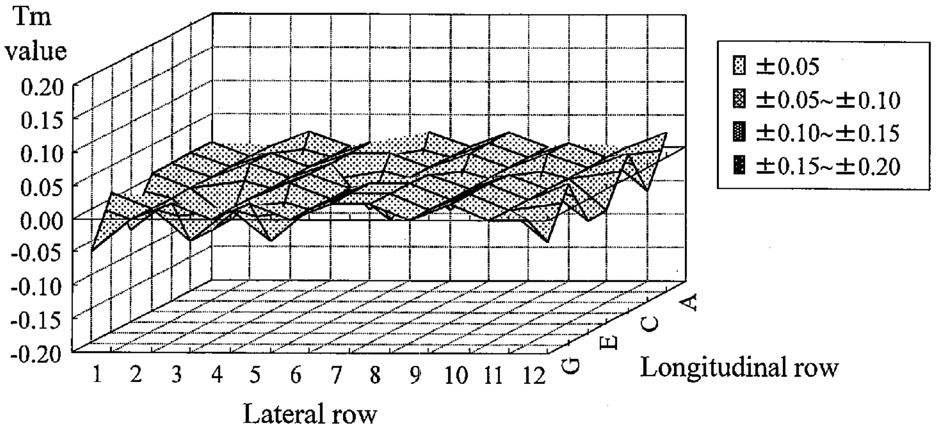
FIG. 1B illustrates the distribution of melting temperature measurement errors between the reaction vessels (wells).

As described above, the nucleic acid amplification system according to the present embodiment is provided with the function of correcting the temperature absolute values of the thermal control blocks 1 by using the temperature calibration sample. Thus, the nucleic acid amplification system according to the present embodiment can make the maximum temperature difference between the thermal control blocks uniform at the same order of precision as the temperature control resolution of the individual thermal control blocks 1. For example, as shown in FIG. 1B, the maximum temperature difference between the thermal control blocks can be made uniform at ±0.05° C. or less. Namely, the temperature difference between the thermal control blocks can be corrected to the same order as the temperature control resolution of the thermal control blocks. Thus, the influence that the difference between the thermal control blocks has on the analysis precision can be disregarded even when nucleic acid amplification is performed by using a plurality of thermal control blocks.

<Embodiment 2>

In the foregoing embodiment, the melting temperature is determined at the part with a large rate of change where the fluorescence intensity is changed sharply (where the fluorescence intensity attenuation rate is the greatest (in the case of FIG. 7B, the fluorescence intensity value is 0.2)).

Figure 8A:
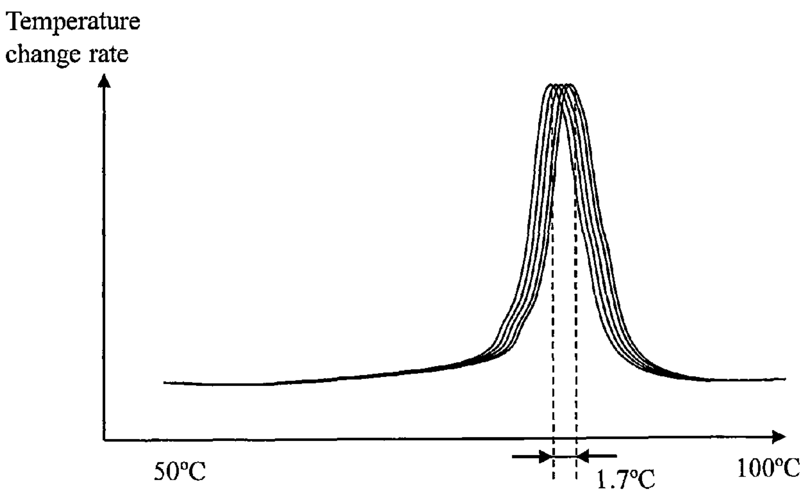
FIG. 8A shows a measurement result in a case where temperature correction was not implemented (before correction).
Figure 8B:
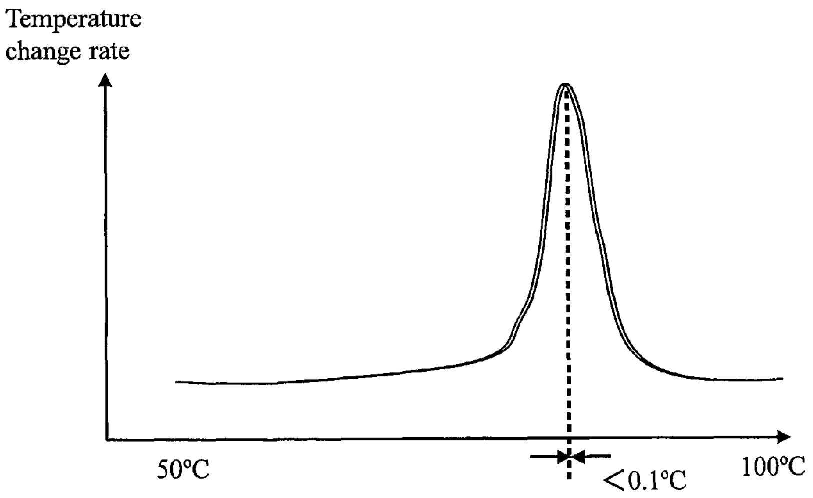
FIG. 8B shows a measurement result in a case where the temperature absolute value of each thermal control block was corrected with reference to the melting temperature.

The melting temperature may be determined by other techniques. For example, the melting temperature may be determined by using a measurement curve plotted with the horizontal axis showing the temperature and the vertical axis showing the fluorescence intensity change rate, as shown in FIGS. 8A and 8B. Specifically, the temperature at which the change in fluorescence intensity is the greatest may be determined as the melting temperature. In this case, the melting temperature can be more clearly identified. FIG. 8A corresponds to FIG. 7A, and FIG. 8B corresponds to FIG. 7B. Obviously, the melting temperature detection is performed by the storage/operating unit 24.

<Embodiment 3>

In the foregoing embodiments, the temperature at which the attenuation rate of the measured fluorescence intensity is the greatest, or the temperature at which the fluorescence intensity change rate is the greatest is used as the melting temperature.

However, for determining the melting temperature, any method may be used as long as the method is capable of determining the melting temperature and is the same as the method used for determining the melting temperature of the temperature calibration sample. Namely, the method is not limited to the method by which the melting temperature is determined from the measurement curve of the temperature calibration sample.

<Embodiment 4>

In the foregoing embodiments, the temperature calibration method that uses the temperature calibration sample with a single melting temperature has been described. Even when the temperature calibration sample has only one melting temperature, the maximum temperature difference of the thermal control blocks 1 can be made uniform at ±0.05° C. or less with respect to temperatures other than the melting temperature, as long as the temperature characteristics of the thermal control blocks 1 are so similar as to be negligible.

However, generally, the individual thermal control blocks 1 have specific temperature characteristics. Thus, according to the present embodiment, the temperature absolute values of the plurality of thermal control blocks are made uniform even when the individually temperature-controllable thermal control blocks 1 are controlled to an arbitrary temperature by adopting a process described below.

Specifically, the temperature characteristics of the individual thermal control blocks 1 are measured in advance and stored in the storage/operating unit 24. When a temperature other than the melting temperature is used for temperature control, the temperatures of the thermal control blocks 1 are controlled based on the temperature characteristics and a control error at the melting temperature. The temperature characteristics may be measured with respect to a temperature range used for nucleic acid amplification. For example, the target temperature may be around 50° C. to around 100° C.

Figure 9:
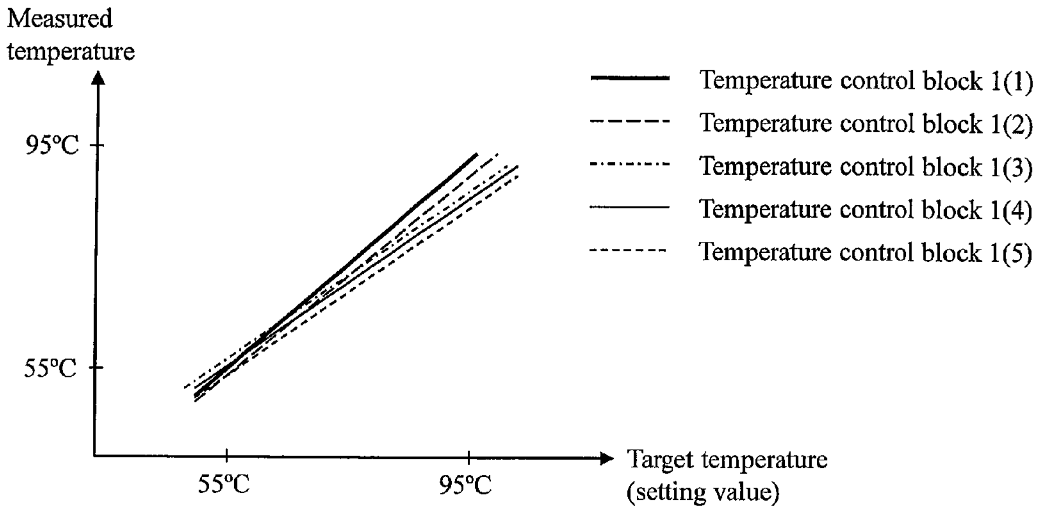
FIG. 9 is a diagram for explaining the specific temperature characteristics of each thermal control block.

FIG. 9 shows an example of temperature characteristics that were actually measured. FIG. 9 shows the temperatures of the thermal control blocks 1 measured by the temperature sensor relative to the target temperature of the thermal control blocks 1 that was varied at 1° C. increments. In FIG. 9, the vertical axis shows the measured temperature and the horizontal axis shows the target temperature. In the case of FIG. 9, the specific temperature characteristics of the individual thermal control blocks 1 can be specified by the slope and intercept of the lines.

Thus, by measuring the specific temperature characteristics of the individual thermal control blocks 1 and storing them in the storage area, and correcting the error between the target temperature and the measured temperature with regard to the melting temperature, each of the thermal control blocks 1 can be accurately controlled to an arbitrary temperature. Namely, the temperature absolute values of a plurality of thermal control blocks can be made uniform with reference to an arbitrary temperature other than the melting temperature.

The temperature characteristics may be measured after temperature correction for the melting temperature. In this case, the relationship between the arbitrary target temperature and the measured temperature is measured. Thus, by using the measured temperature characteristics as is, the thermal control blocks 1 can be controlled to an arbitrary temperature absolute value.

<Embodiment 5>

In the following, a temperature correction function for evaluating temperature precision after the correction will be described. Ideally, at the end of the above-described temperature correction, the measured melting temperature of the temperature control blocks 1 should match the reference melting temperature (Strictly, the difference should be on the same order as the temperature control resolution, or smaller). However, due to device failure and the like, an error may remain even after the temperature correction. Thus, the temperature correction function described below is proposed.

Figure 10:
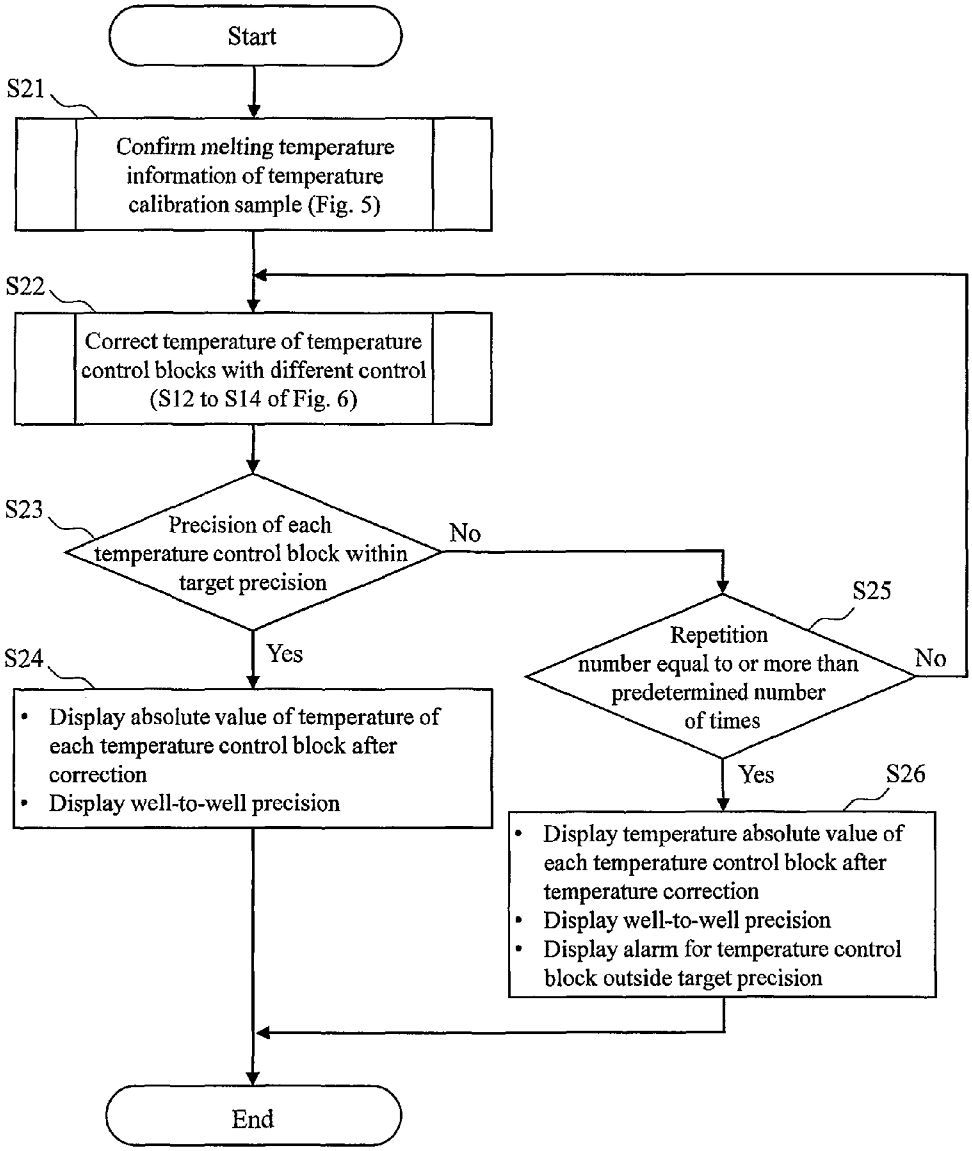
FIG. 10 is a diagram for explaining a temperature correction operation including the function of evaluating temperature precision after correction.

FIG. 10 shows a process procedure example corresponding to the temperature correction function. First, the storage/operating unit 24 performs the reference melting temperature confirming process as described above (step S21). This processing operation is the same as steps S1 to S4 of FIG. 5.

Next, the storage/operating unit 24 performs temperature correction of the thermal control blocks 1 (step S22). This processing operation is the same as steps S12 to S14 of FIG. 6. Specifically, the target temperature of the temperature control blocks 1 is varied from around 50° C. to around 100° C., and the melting temperature measurement and the temperature absolute value correction are performed.

When the temperature correction of step S22 is completed, the storage/operating unit 24 measures the melting temperature of the temperature calibration sample for the thermal control blocks 1 again. This operation is automatically performed. At this time, the storage/operating unit 24 determines whether the temperature difference between the measured melting temperature and the reference melting temperature is within a target precision (i.e., whether equal to or less than a determination threshold value) (step S23). The threshold value for the target precision may be set by the user in advance, or allocated as an initial value.

When the temperature difference is determined to be within the target precision, the storage/operating unit 24 causes the precision satisfied by the thermal control blocks 1 to be displayed, and ends the correction operation (step S24). When the precision is displayed, the measured temperature absolute values of the thermal control blocks 1 after correction, and well-to-well precision may also be displayed.

On the other hand, when it is determined in step S23 that the temperature difference exceeds the target precision, the storage/operating unit 24 compares the number of times of temperature correction that has been already performed (repetition number) and a threshold value (step S25). The threshold value provides the upper-limit value of the number of times of the melting temperature measurement and the correction of the temperature absolute value of the thermal control blocks 1. The threshold value may be set by the user in advance, or may be allocated as an initial value.

When there is a thermal control block 1 for which a negative result is obtained in the determination process of step S25 (i.e., the number of times of temperature correction for the thermal control block has not reached the predetermined threshold value), the storage/operating unit 24 returns to step S22.

The storage/operating unit 24 performs, for each of the thermal control blocks 1, the temperature absolute value correction process based on the temperature difference between the measurement value of the melting temperature and the correct melting temperature. When there is a thermal control block that does not fall within the target precision, the series of operations is repeatedly performed until a specified repetition number is reached.

If the temperature control precision of the thermal control block does not fall within the target precision even after the series of operations is repeated by the specified number of times (i.e., a positive result is obtained in step S25), the storage/operating unit 24 identifies the relevant thermal control block 1, and causes an alarm indicating temperature control abnormality to be displayed (step S26). In this case, too, the storage/operating unit 24 causes the measured temperature absolute values of the temperature control blocks 1 after correction and the well-to-well precision to be displayed.

In a more preferred embodiment, even during a normal operation performed after the correction operation, the alarm indicating temperature control abnormality may be displayed constantly with respect to the thermal control block that does not fall within the target precision. The "normal operation" may refer to any of operations that the nucleic acid amplification system can perform, other than the system operation for temperature calibration. In a more preferred embodiment, control such that the thermal control block in which temperature control abnormality is detected is automatically removed from the object of the normal operation may be implemented.

<Embodiment 6>

In the foregoing embodiments, the nucleic acid amplification system provided with the temperature correction function that assumes the use of a single type of temperature calibration sample has been described.

In the following, on the assumption that two types of temperature calibration samples are used, the nucleic acid amplification system provided with the function of correcting the temperature absolute values of the individually temperature-controllable thermal control blocks 1 will be described. The nucleic acid amplification system according to the present embodiment has a basic configuration similar to that of the nucleic acid amplification system described with reference to Embodiment 1.

According to the present embodiment, the two types of temperature calibration samples may have melting temperatures separated by at least 5° C. More preferably, as the first type of temperature calibration sample, a nucleic acid fragment with the melting temperature of around 60° C. (such as 50° C. to 70° C.) may be used, and as the second type of temperature calibration sample, a nucleic acid fragment with the melting temperature of around 90° C. (such as 80° C. to 100° C.) may be used. The temperature calibration samples may be measured separately to determine the melting temperatures, or the two melting temperatures may be measured simultaneously in a single melting temperature measurement using a mixture solution of the temperature calibration samples.

Figure 11:
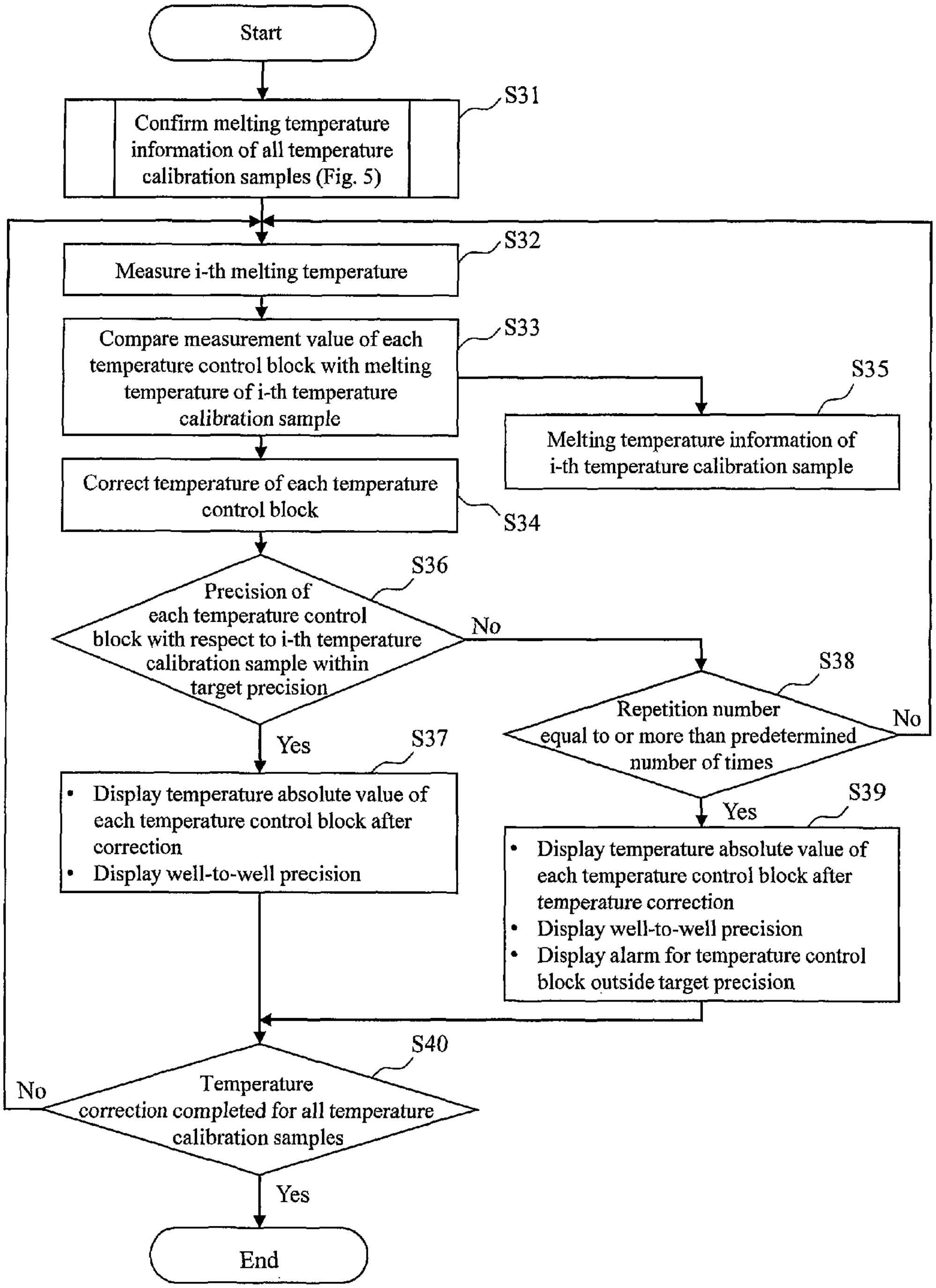
FIG. 11 is a diagram for explaining the temperature correction operation using a plurality of temperature calibration samples.

FIG. 11 shows a process procedure example corresponding to the temperature correction function using N (N≥2) temperature calibration samples. In the case of FIG. 11, in view of the fact that the plurality of individually temperature-controllable thermal control blocks 1 have different temperature characteristics, the determination of an optimum correction value for each of the temperature calibration samples and calibration are repeated.

First, the storage/operating unit 24 performs a process of confirming all of the N items of melting temperature information (step S31). This processing operation is the same as steps S1 to S4 of FIG. 5 with the exception that the number of the melting temperatures confirmed is N.

Next, the storage/operating unit 24 variably controls the target temperature for each of the thermal control blocks 1, and actually measures the temperature of the temperature control blocks 1 at the point in time of detection of the melting temperature of the i-th temperature calibration sample (i=1, 2, . . . , N) (step S32).

Then, the storage/operating unit 24 compares the actually measured melting temperature with the correct melting temperature of the i-th temperature calibration sample (step S33). Also, the storage/operating unit 24 causes the correct melting temperature information of the i-th temperature calibration sample that has been acquired in advance to be displayed (step S35).

Thereafter, the storage/operating unit 24 corrects the temperature absolute value of each of the thermal control blocks 1 such that the melting temperatures actually measured for each of the thermal control blocks 1 matches the correct melting temperature (step S34).

The storage/operating unit 24 then measures the melting temperature of the i-th temperature calibration sample for each of the thermal control blocks 1, and determines whether the difference value between the measured melting temperature and the reference melting temperature is within a target precision (step S36).

If it is determined that the difference value is within the target precision, the storage/operating unit 24 causes the precision satisfied by the thermal control blocks to be displayed, and proceeds to a process for the next temperature calibration sample (step S37). Specifically, the measured temperature absolute values of the thermal control blocks 1 after correction and the well-to-well precision are displayed.

On the other hand, when it is determined in step S36 that the temperature difference exceeds the target precision, the storage/operating unit 24 compares the number of times of temperature correction that has already been performed (repetition number) and a threshold value (step S38).

If there is a thermal control block 1 for which a negative result is obtained in the determination process of step S38 (i.e., when the number of times of temperature correction for the relevant thermal control block has not reached the predetermined threshold value), the storage/operating unit 24 returns to step S32.

Thereafter, the storage/operating unit 24 performs, for each of the thermal control blocks 1, the temperature absolute value correction process based on the temperature difference between the melting temperature measurement value and the correct melting temperature again. When the temperature difference between the thermal control blocks is not within a target precision, the series of operations is repeatedly performed until the specified repetition number is reached.

If the precision between the thermal control blocks does not fall within the target precision after the series of operations is repeated by the specified number of times (i.e., when a positive result is obtained in step S38), the storage/operating unit 24 identifies the relevant thermal control block 1, and causes an alarm indicating temperature control abnormality to be displayed (step S39).

After step S37 or step S39, the storage/operating unit 24 determines whether the correction operation has been completed for all of the temperature calibration samples (step S40). If a negative result is obtained, the storage/operating unit 24 returns to step S32, and performs the correction operation for the next i+1 th temperature calibration sample. When a positive result is obtained in step S40, the series of processes ends.

<Embodiment 7>

(Functional Block Configuration of Genetic Testing System)

In the following, a genetic testing system incorporating the nucleic acid amplification system according to the foregoing embodiments will be described. An example of the genetic testing system is a genetic testing apparatus.

(Specific Example 1 of Apparatus Configuration)

Figure 12:
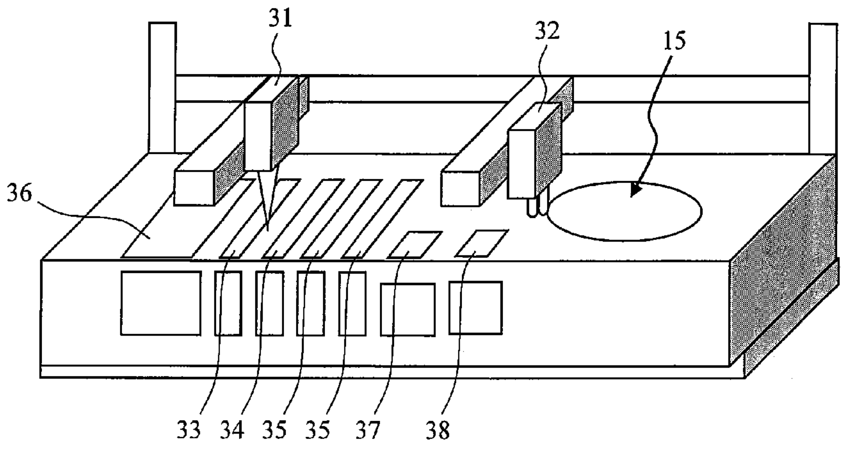
FIG. 12 illustrates a configuration example of an automatic analysis apparatus incorporating a real-time fluorescence measurement mechanism.

FIG. 12 illustrates a specific example of the genetic testing system according to the present embodiment. The genetic testing system includes a preprocessing unit, a real-time fluorescence measurement mechanism 15, and a control unit which is not shown. The preprocessing unit includes at least a dispensing mechanism 31, a reaction vessel transport mechanism 32, a sample mount position 33, a nucleic acid extracting reagent mount position 34, a nucleic acid amplification reagent mount position 35, an expendable supplies mount position 36, an expendable supplies disposing opening 37, and a reaction vessel disposing opening 38. The dispensing mechanism 31 is fitted with a dispenser tip for dispensing a reagent or a sample. The apparatus configuration illustrated in FIG. 12 corresponds to a case where the real-time fluorescence measurement mechanism 15 of the configuration illustrated in FIG. 3 is incorporated; namely, the case where the real-time fluorescence measurement mechanism 15 with the rotating drive system is used.

(Specific Example 2 of Apparatus Configuration)

Figure 13:
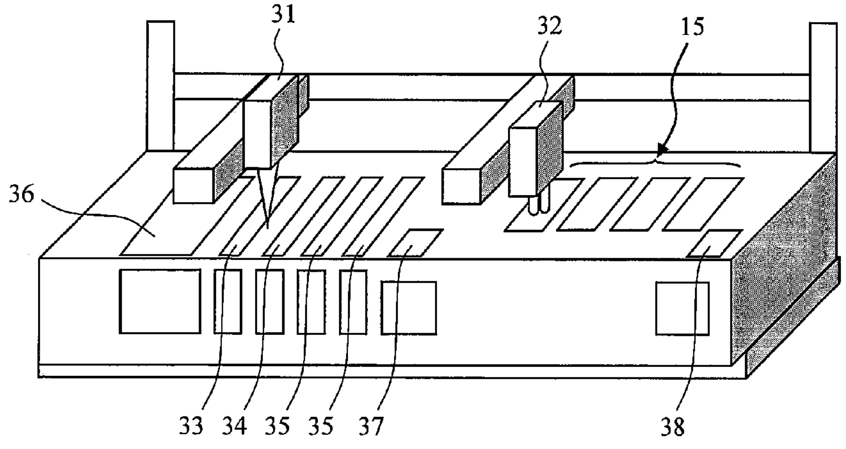
FIG. 13 illustrates a configuration example of the automatic analysis apparatus incorporating the real-time fluorescence measurement mechanism.

FIG. 13 illustrates another specific example of the genetic testing system according to the present embodiment. The genetic testing system illustrated in FIG. 13 corresponds to a case where the real-time fluorescence measurement mechanism 15 of the configuration illustrated in FIG. 4 is incorporated; namely, the case where the real-time fluorescence measurement mechanism 15 without a rotating drive system is used.

(Processing Operation)

Figure 14:
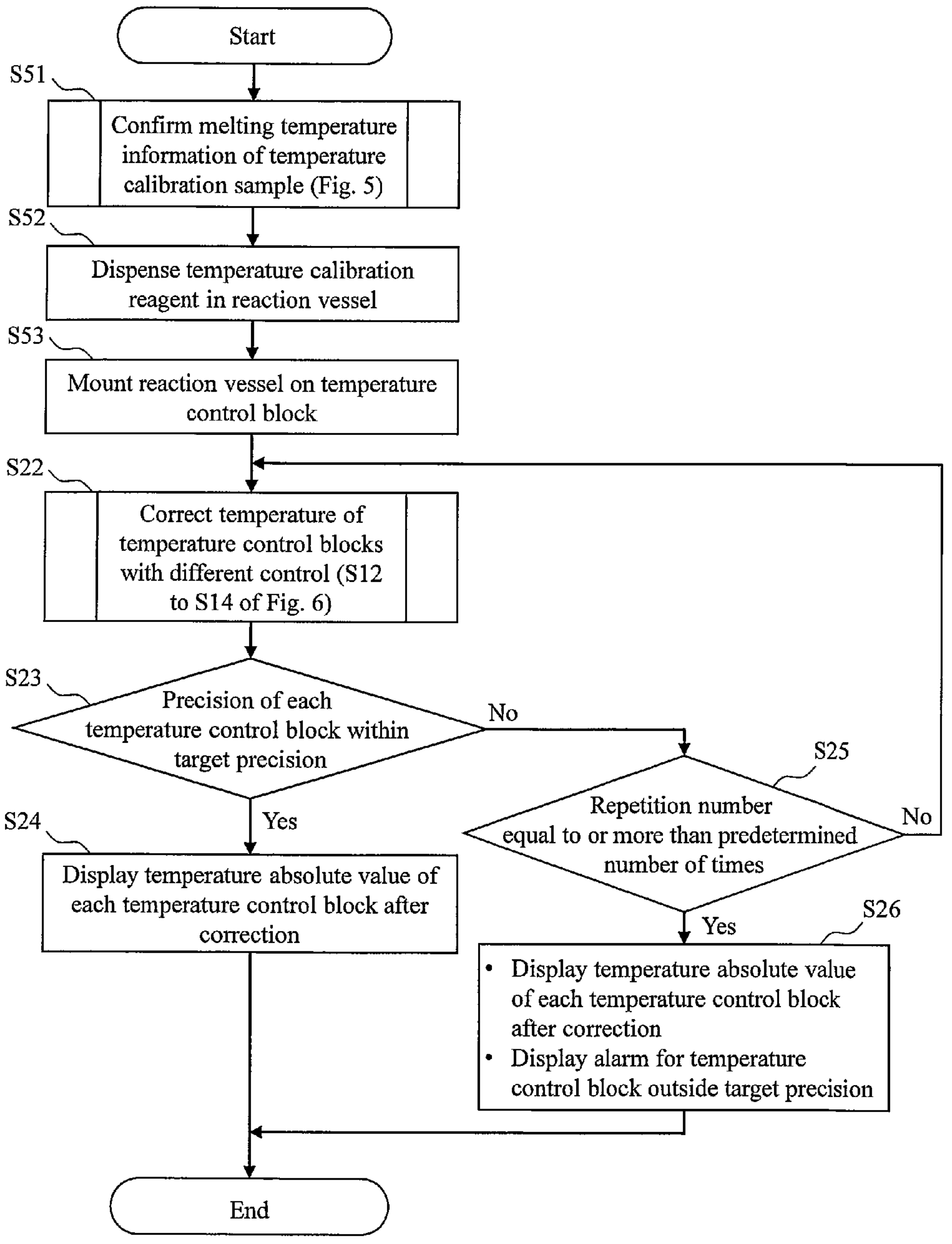
FIG. 14 is a diagram for explaining a processing operation of a genetic testing system.

FIG. 14 shows a processing operation procedure performed in the genetic testing system illustrated in FIG. 12 or 13. In FIG. 14, parts corresponding to the parts of FIG. 10 are designated with similar reference signs.

First, a user mounts a temperature calibration reagent and expendable supplies required for an operation of the genetic testing system at predetermined positions. The user then inputs instructions for temperature correction or temperature confirmation of the individually temperature-controllable thermal control blocks 1.

Upon detection of the instruction inputs, the genetic testing system confirms the melting temperature of the temperature calibration reagent, and stores the melting temperature in the storage area (step S51). The melting temperature may be entered into the genetic testing system via a network and/or from a bar-code affixed to the temperature calibration reagent vessel, or manually by the user.

Next, the dispensing mechanism 31 dispenses a predetermined amount of the temperature calibration sample mounted on the reagent mount position 33 into the reaction vessel (step S52). The predetermined amount may be of any volume as long as it can be measured by the real-time fluorescence measurement mechanism 15. Preferably, when the real-time fluorescence measurement mechanism 15 is not provided with a reaction solution evaporation preventing function, mineral oil may be added onto the upper layer of the temperature calibration sample at this stage.

Thereafter, the reaction vessel is capped, and transported to the real-time fluorescence measurement mechanism 15 via the reaction vessel transport mechanism 32. Then, the temperature correction operation according to the foregoing embodiments is performed (steps S22 to S26).

Figure 15A:
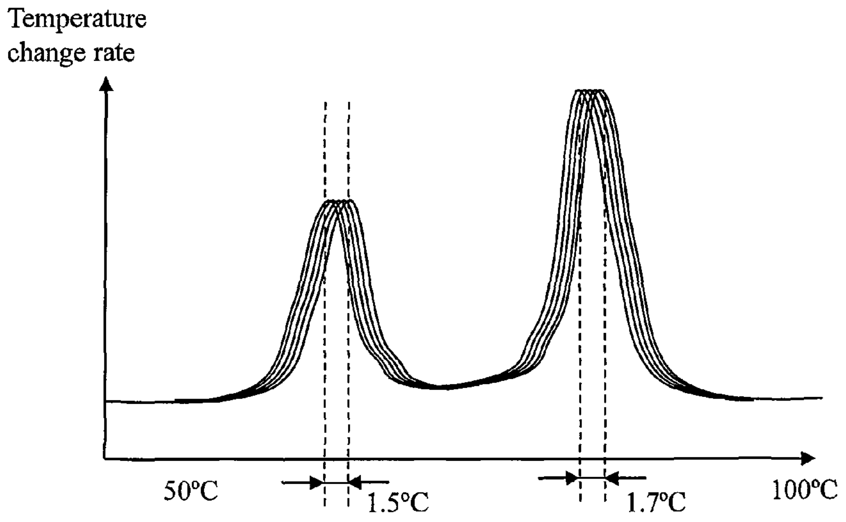
FIG. 15A shows a measurement result in a case where temperature correction is not implemented (before correction).

FIG. 15A shows a measurement example of the melting temperature curve of the thermal control blocks 1 when no temperature correction at all is performed. The measurement example of the melting temperature curve shown in FIG. 15A is that of a case where the melting temperature is measured with regard to a mixture solution of two types of temperature calibration samples (such as samples having a low-temperature side melting temperature (60° C.) and a high-temperature side melting temperature (95° C.)). In FIG. 15A, the horizontal axis shows the temperature, and the vertical axis shows the temperature change rate. As shown, when no temperature correction is performed, a maximum temperature difference of 1.5° C. is observed for the low-temperature side melting temperature, while a maximum temperature difference of 1.7° C. is observed for the high-temperature side melting temperature.

Figure 15B:
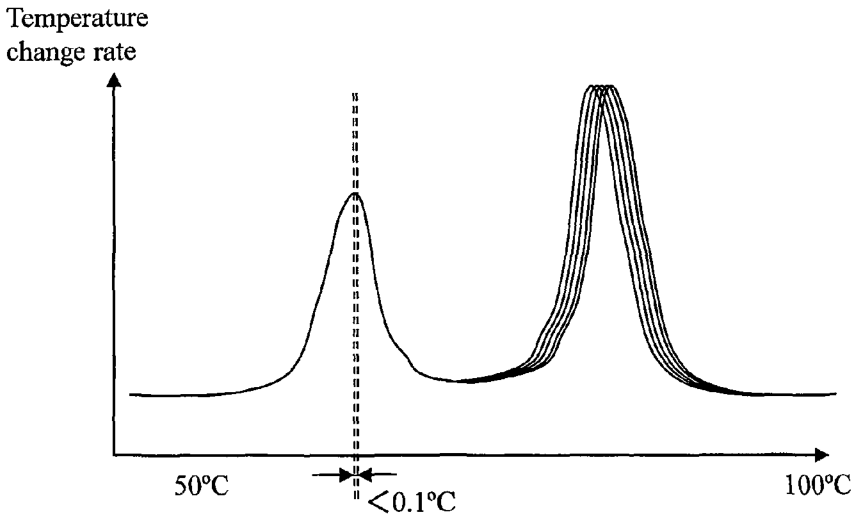
FIG. 15B shows a measurement result in a case where the temperature absolute value of each thermal control block was corrected with reference to a melting temperature on low-temperature side.
Figure 15C:
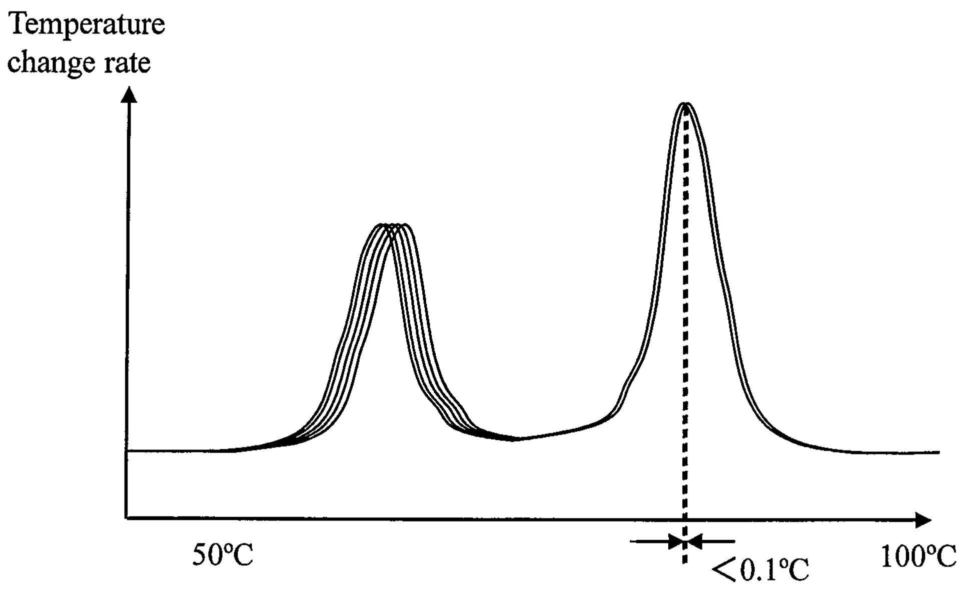
FIG. 15C shows a measurement result in a case where the temperature absolute value of each thermal control block was corrected with reference to a melting temperature on high-temperature side.

On the other hand, when temperature correction is performed with reference to the melting temperature, as shown in FIGS. 15B and 15C, the temperature difference between the thermal control blocks can be controlled to be 0.1° C. or less. FIG. 15B shows a melting temperature curve measured when the temperature of the thermal control blocks 1 was corrected with respect to the low-temperature side melting temperature, and FIG. 15C shows a melting temperature curve measured when the temperature of the thermal control blocks 1 was corrected with respect to the high-temperature side melting temperature.

In either case, the temperature absolute values of the thermal control blocks 1 can be aligned to the melting temperature, whereby a very high uniformity compared with conventional techniques can be obtained. Further, by incorporating the target precision evaluation function, the temperature control block 1 with abnormal fluid temperature control can be automatically identified. By storing the information about the thermal control block 1 for which temperature control abnormality has been identified on the system side, control such that the thermal control block 1 with the recognized temperature control abnormality is removed from the testing area during normal testing or the testing result is not used can be implemented.

<Embodiment 8>

In the foregoing description of embodiments, the temperature absolute values of a plurality of thermal control blocks are made uniform within a single nucleic acid amplification system or genetic testing system.

In the following, a system configuration suitable for a case where the temperature absolute values are made uniform between a plurality of nucleic acid amplification systems or genetic testing systems will be described.

Figure 16:
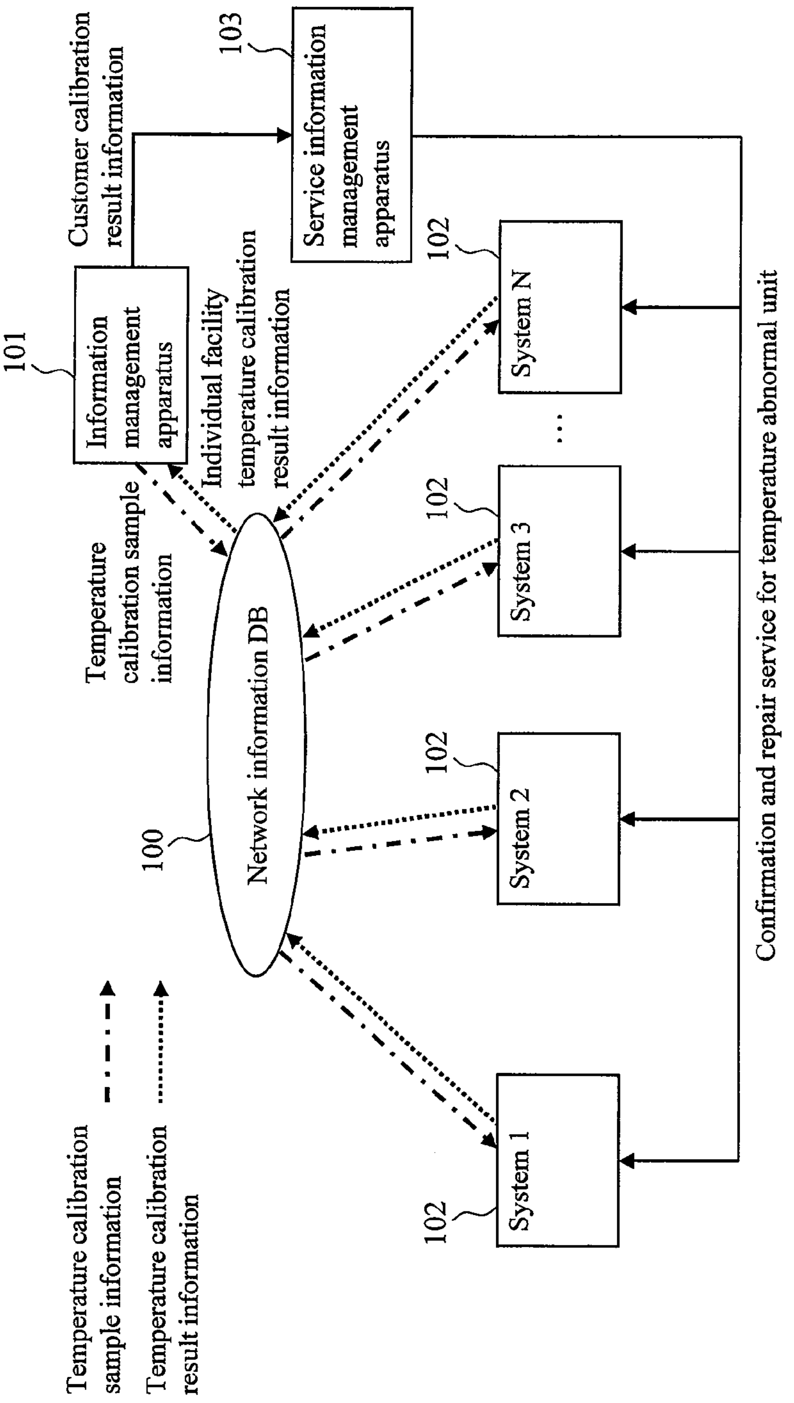
FIG. 16 is a diagram for explaining a network system configuration.

FIG. 16 shows a system configuration according to the present embodiment. Of course, in this embodiment, too, a temperature calibration sample is used for temperature correction. The system shown in FIG. 16 includes a network information data base 100, an information management apparatus 101, nucleic acid amplification systems 102, and a service information management apparatus 103.

In the network information data base 100, temperature calibration sample information (specifically, melting temperature of the temperature calibration sample), and temperature calibration result information of each of the nucleic acid amplification systems 102 are stored. The temperature calibration sample information is stored in the network information data base 100 from the information management apparatus 101 via a network, and read by the N nucleic acid amplification systems 102 via the network. The temperature calibration result information is stored in the network information data base 100 from the N nucleic acid amplification systems 102 via the network, and read by the information management apparatus 101.

A temperature correction operation using the temperature calibration sample with the same melting temperature is performed by the nucleic acid amplification systems 102, so that the temperature absolute values of the N systems can be made uniform. Further, the information management apparatus 101 can centrally manage the temperature calibration result information of the nucleic acid amplification systems 102. Thus, when temperature control abnormality is recognized in one of the nucleic acid amplification systems 102, information about the nucleic acid amplification system 102 in which the abnormality has been discovered can be supplied to the service information management apparatus 103 managing service information, thereby enabling quick customer support. Of course, the service information management apparatus 103 and the nucleic acid amplification systems 102 as service provided locations may be disposed at the same or different positions.

<Other Embodiment>

The present invention is not limited to the foregoing embodiments, and may include various modifications. The foregoing embodiments have been described in detail to facilitate an understanding of the present invention, and the present invention is not necessarily limited to embodiments having all of the configurations described. A part of one embodiment may be substituted by a configuration of another embodiment, or a configuration of the other embodiment may be incorporated into a configuration of the one embodiment. With regard to a part of the configuration of an embodiment, additions, deletions, or substitutions may be made.

The configurations, functions, processing units, process means and the like described above may be partly or entirely implemented in the form of hardware, such as an integrated circuit. The configurations, functions and the like described above may be implemented in the form of software, such as a program interpreted and executed by a processor to implement the respective functions. Programs, tables, files, and other information for implementing the respective functions may be stored in a recording unit such as a memory, a hard disk, or a solid state drive (SSD), or in a recording medium such as an IC card, an SD card, or a DVD.

Further, control lines and information lines that are illustrated in the foregoing embodiments are only those considered necessary for purposes of explanation, and do not necessarily represent all of the control lines or information lines required in a product. All of the configurations may be mutually connected.

REFERENCE SIGNS LIST

1 Thermal control block
3 Real-time fluorescence measuring unit
5 Control unit
7 Melting temperature measurement unit
9 Temperature correction unit
11 Storage unit
15 Real-time fluorescence measurement mechanism
21 Reaction vessel
22 Rotary disc
23 Data processing unit
24 Storage/operating unit
25 System control unit
26 Reaction plate
31 Dispensing mechanism
32 Reaction vessel transport mechanism
33 Sample mount position
34 Nucleic acid extracting reagent mount position
35 Nucleic acid amplification reagent mount position
36 Expendable supplies mount position
37 Expendable supplies disposing opening
38 Reaction vessel disposing opening
100 Network information data base
101 Information management apparatus
102 Nucleic acid amplification system
103 Service information management apparatus

The invention claimed is:

1. A testing system comprising:

a network information database;

an information management apparatus connected to the network information database;

two or more genetic testing systems each including a plurality of temperature control units, the genetic testing systems being connected via a network to the network information database; and a service management apparatus connected to the information management apparatus and to the genetic testing systems via the network, wherein the information management apparatus:

distributes temperature calibration sample information via the network information database to the two or more genetic testing systems, automatically identifies one of the temperature control units with abnormal fluid temperature control in one of the two or more genetic testing systems, controls the two or more genetic testing systems such that the one of the temperature control units with the abnormal fluid temperature control is removed from a testing area during normal testing or a testing result thereof is not used, and supplies information about the one of the two or more genetic testing systems which has the one of the temperature control units with the abnormal fluid temperature control to the service information management apparatus when the abnormal fluid temperature control is identified, wherein each of the two or more genetic testing systems receives the same temperature calibration sample information and compares the temperature calibration sample information with a measured temperature obtained by performing a predetermined temperature calibration with the plurality of temperature control units of each of the two or more genetic testing systems, and wherein the temperature control units of each of the two or more genetic testing systems correct the measured temperature to be substantially the same temperature in each of the two or more genetic testing systems.

2. The testing system according to claim 1, wherein the predetermined temperature calibration includes measurement of a melting temperature of a temperature calibration sample as the measured temperature.

3. The testing system according to claim 1, wherein the service information management apparatus receives temperature calibration result information of each of the genetic testing systems connected via the network via the information management apparatus, and wherein the information management apparatus centrally manages the temperature calibration result information of the genetic testing systems.

4. The testing system according to claim 1, wherein the temperature calibration sample information is a melting temperature of a temperature calibration sample.

* * * * *